United States Patent [19]

Will

[11] Patent Number: 4,905,694
[45] Date of Patent: Mar. 6, 1990

[54] INTRACORPOREAL TEMPORARY WOUND CLOSURE

[75] Inventor: Fritz Will, Hasselbusch, Fed. Rep. of Germany

[73] Assignee: Ethicon, Inc., Somerville, N.J.

[21] Appl. No.: 333,509

[22] Filed: Apr. 4, 1989

Related U.S. Application Data

[63] Continuation-in-part of Ser. No. 252,318, Oct. 3, 1988, abandoned, which is a continuation of Ser. No. 115,299, Nov. 25, 1987, abandoned, which is a continuation-in-part of Ser. No. 850,653, Apr. 11, 1986, abandoned.

[51] Int. Cl.$^4$ .................. A61B 17/08; A44B 19/00
[52] U.S. Cl. ........................ 606/217; 24/390; 24/400
[58] Field of Search .................. 128/335; 24/390, 400

[56] References Cited

U.S. PATENT DOCUMENTS

| | | | |
|---|---|---|---|
| 2,012,755 | 8/1935 | De Muth | 128/335 |
| 2,259,495 | 10/1941 | Soaye | 24/390 |
| 2,665,467 | 1/1954 | Bosomworth et al. | 24/400 |
| 3,516,409 | 6/1970 | Howell | 128/335 |

Primary Examiner—Edward M. Coven
Assistant Examiner—Gary Jackson
Attorney, Agent, or Firm—Robert L. Minier

[57] ABSTRACT

The invention relates to a temporary wound closure for intracorporeal use comprising two strip-shaped sheets which are made from a sewable material coated at least in zones with plastics and whose zones overlapping in the closed condition are provided with interengaging profiled closure strips which can be brought into engagement by a clamping pusher, the strip-shaped sheet which is at the bottom in the closed condition having beneath its profiled closure strip a sealing or underengaging strip extending over the whole closure zone.

2 Claims, 3 Drawing Sheets

INTRACORPOREAL TEMPORARY WOUND CLOSURE

RELATED APPLICATIONS

The present application is a Continuation-in-Part patent application of copending patent application Ser. No. 252,318 filed Oct. 3, 1988, which is a continuation of application Ser. No. 115,299 filed Nov. 25, 1987 which is a continuation-in-part application of Ser. No. 850,653 filed Apr. 11, 1986 all abandoned.

BACKGROUND OF THE INVENTION

The invention relates to a temporary wound closure for intracorporeal use; i.e. use within the body.

In surgery wounds may have to be closed only temporarily. For example, in the case of diffuse purulent peritonitis the abdominal cavity must be regularly flushed out with a disinfecting solution, for example, a chloramine solution, whereafter the wound is closed only provisionally with rough stitches or gauzes until the next flushing. Staged washing therapy of that kind is able to reduce the mortality rate of diffuse purulent peritonitis, which is today still very high, to about 20%.

Temporary wound closures are also required with the decomposition of the pancreas, when under certain conditions the pancreas may gradually become necrotic. Since the necrotic tissue must be removed immediately, the abdomen is conveniently opened on each occasion within a number of periods of time, to give the patient a better chance of survival.

Finally, intracorporeal temporary wound closures are always advantageous if there is a suspicion that postoperational difficulties may occur.

More particularly in the case of washing at intervals, an attempt has been made to sew ordinary zip fasteners after sterilization into the human body as a temporary wound closure.

There is the risk that body fluid may emerge through the individual teeth of the zip fastener, or that body tissue will get jammed and damaged between the teeth of the fastener. Moreover, the narrow edges of ordinary zip fasteners cannot be satisfactorily sewed to the adjacent tissue, and since moreover the fastener must be sewn in the open condition, it cannot always be correctly aligned and adequately closed.

While fasteners have been developed, such as described in U.S. Pat. No. 2,665,467, which do not have individual teeth as does the common zip fastener, these fasteners are still not suitable for intracorporeal use. These fasteners still cannot be adequately attached to adjacent tissue and still do not provide the desired hermetic seal for intracorporeal use. Furthermore, while there are not individual teeth on which tissue can be caught, the profiled closing strips still may engage and damage tissue during the closing of the wound and fastener.

In some surgical dressings, for example, as shown in U.S. Pat. No. 2,012,755, developments have been made to prevent the fastener from damaging the skin. In this patent a plastic strip is placed beneath the zig fastener to prevent the pinching of skin r tissue when the fastener is opened and closed. However, such surgical dressings are not suitable for intracorporeal use because it is desired that they not form a hermetic seal but, in fact, allows for drainage of the wound. Furthermore, such dressings are not sutured or sewn to the adjacent tissue but are usually applied with a pressure sensitive adhesive. The use of a pressure sensitive adhesive intracorporeal is not desired for a number of reasons, such as lack of bio-compatibility and failure to provide the desired adhesive to body tissue when placed in the intracorporeal environment.

Other zip fasteners such as, for example, those of divers' suits, would in fact theoretically produce a hermetic closure, but they are too heavy and also have the aforementioned disadvantages when sewn in open.

Furthermore, standard types of adhesive surgical dressings which are used on the skin or outside the body are unsatisfactory for intracorporeal use for a number of reasons. Such closures do not always provide a leakproof seal, are difficult to align longitudinally and most importantly cannot be readjusted in order to compensate for the swelling and/or shrinkage of a traumatized portion of the human body. Also, such adhesive surgical dressings suffer from lack of desired bio-compatibility and failure to provide assured adherence to tissue intracorporeally.

It is an object of the invention to provide a temporary wound closure for intracorporeal use which is bio-compatible, which can be very simply connected to the fascia or abdomen covering, can be connected to tissue with the desired assured correction, can be so connected a number of times, causes no damage to the tissue, can be sewn in open, has closure zones sliding against one another, provides for longitudinal alignment and is fluid-tight.

DESCRIPTION OF INVENTION

The wound closure of the present invention comprises two sheets of a sterilizable material which can be sewn to the fascia, abdomen covering or similar intracorporeal body tissue and; preferably a fabric or a fleece which is coated at least in zones with plastic material. Provided at the end zones of the sheets, overlapping in the closed condition, are interengaging profiled closure strips which can be brought into engagement by a clamping pusher. The closure strips are preferably made of Polyethylene and can be readily welded to the plastics coating of the sheets. Disposed beneath the profiled closure strip is a sealing or underengaging strip which extends under the closure zone and can be unitary with the sheet retaining the profiled closure strip.

The profiled closure strips can be of any required cross-sectional shape; the only essential thing is that the profiles must be designed to engage in one another in a continuous manner; in the simplest case they can be U-shaped or W-shaped

DETAILED DESCRIPTION OF THE INVENTION

The invention will now be described in greater detail with reference to the drawings, wherein.

Figure 1:
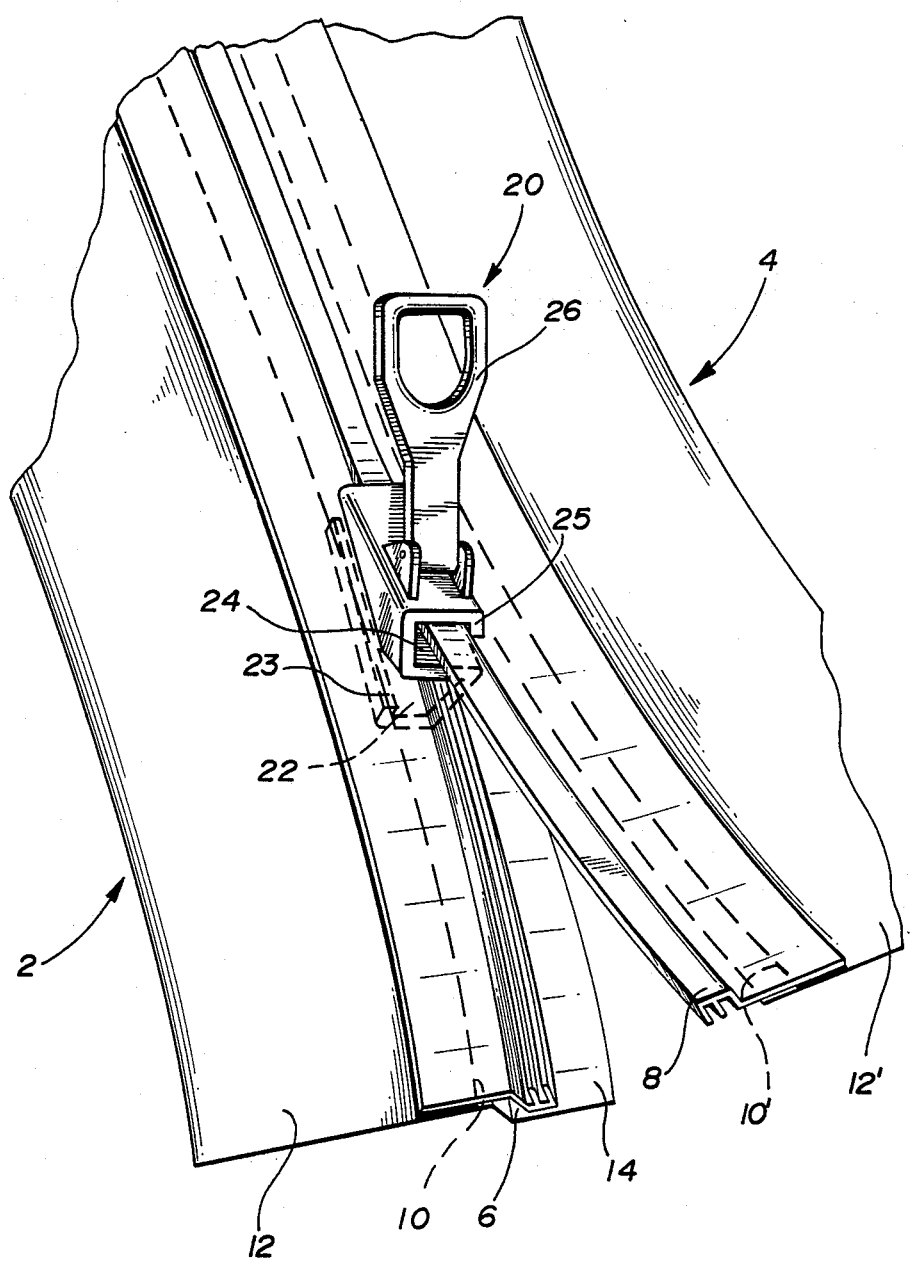
FIG. 1 is a view of a partially opened wound closure according to the invention
Figure 4:
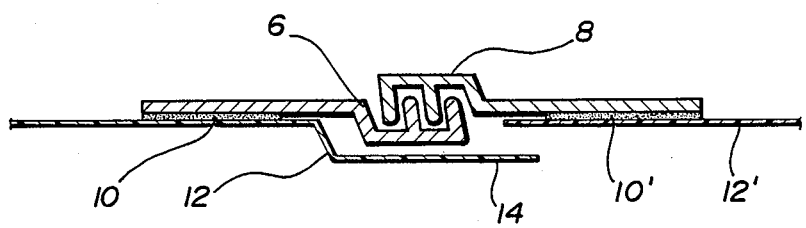
FIG. 4 is a cross-section through the wound closure.

The wound closure comprises two strip-shaped sheets 2 and 4 of substantially identical size which are made from a sewable material, in the present instance a polyester fabric coated with polyethylene. Exactly like the sheet 4 shown on the right in FIG. 1, the sheet 2 shown on the left has in its edge zone a profiled closure strip 6;8 of polyethylene, which are welded via a welding seam 10;10' to fabric strip 12 of sheet 2 and fabric strip 12' of sheet 4 respectively. While in the case of fabric strip 12' the welding seam 10' lies directly in the edge zone of the sheet 4 or of the strip 12', the profiled strip 6 of the left-hand sheet 2 is so sealed on to the fabric strip 12 at a distance from the edge thereof, that the result is a sealing or underengaging strip 14. As more clearly shown in FIG. 4, the underengaging strip 14 is integral as part of fabric strip 12 and extends past the edge of fabric strip 12' so as to provide the desired seal.

Figure 2:
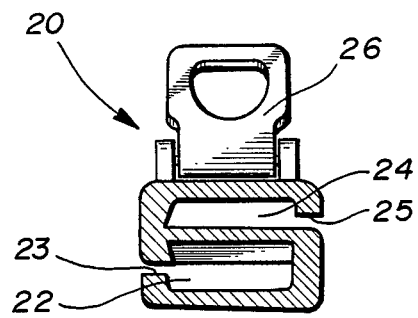
FIG. 2 is a cross-section through the pusher of the wound closure.
Figure 3:
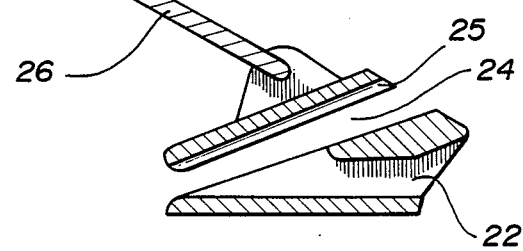
FIG. 3 is a longitudinal section through the pusher of the wound closure.

The pusher 20 shown in cross-section and longitudinal section in FIGS. 2 and 3 respectively has on the threading-in side a substantially S-shaped cross-section, so that a lower threading-in chamber 22 and an upper threading-in chamber 24 are formed, whose opposite sides each have a guide web member 23 and 25 respectively. The threading-in chambers come together substantially at the centre of the pusher, while at the same time the difference in height between the top and bottom wall of the pusher is reduced to such an extent that when the pusher is pulled through, the profiles of the profiled strips are forced into sealing engagement. The pusher 20 also has a handle 26 of suitable shape.

Figure 5A:
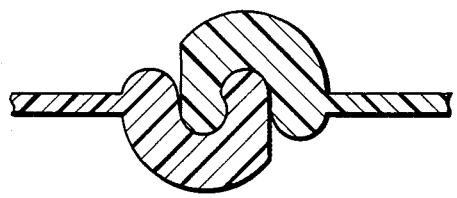
FIGS. 5a to 5c are cross-sectional profiles of the closure strips.
Figure 5B:
Figure 5C:
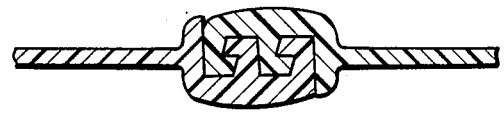

FIGS. 5a to c are cross-sections through different profiles for the profiled closure strips.

The two strip-shaped sheets or fabric strips are preferably about 50 cm long. The width of the strips, measured from the outer edge to the profiled closure strip, is preferably 5 to 6 cm, while the overlapping part of the sealing or underengaging strip can be about 1.5 to 2.5 cm in width.

Since the material is cuttable, the operator can cut the closure to the required length as needed and decide how to closely the closure must be sewn in. For example, both sheets or fabric strips can be sewn to the fascia in the area of the wound, and then closed after the profiled closure strips have been threaded into the pusher. Particularly advantageously, the two strips can slide in relation to one another parallel with the profiled closure strips even in the closed condition, so that no unnecessary stresses are created in the area of the wound.

All of the materials used in providing the intercorporeal wound closure devices of the present invention have sufficient bio-compatability with human tissue so as to be safe for intracorporeal use.

I claim:

1. A bio-compatible temporary wound closure device for the intracorporeal closing of a surgical wound, said device comprising, two strip-shaped sheets, said sheets being of a sewable polyester fabric, a portion of said polyester fabric being coated with a plastic material to form a fluid impervious zone, said coated portions overlapping when the device is in the closed condition, said coated portions being provided with interengaging profiled closure strips which can be brought into engagement by a clamping pusher, the strip shaped sheet disposed at the bottom of the device, when the device is in the closed condition, having disposed beneath its closure strip a sealing or underengaging strip, said underengaging strip being an integral part of the strip shaped sheet disposed at the bottom of the device, said sealing or underengaging strip extending over the whole closure zone and disposed to contact said surgical wound whereby a fluid tight closure may be attained.

2. A wound closure device according to claim 1, characterized that the strip-shaped sheets have a width of at least 4 cm. and the sealing or underengaging strip is at least 1 cm. wide.

* * * * *